United States Patent [19]

Kita et al.

[11] 4,101,403

[45] Jul. 18, 1978

[54] SENSOR FOR DETECTING VARIATION IN OXYGEN CONCENTRATION IN GAS

[75] Inventors: Toru Kita; Takeshi Fujishiro, both of Yokohama, Japan

[73] Assignee: Nissan Motor Company, Limited, Japan

[21] Appl. No.: 749,899

[22] Filed: Dec. 13, 1976

[30] Foreign Application Priority Data

Dec. 18, 1975 [JP] Japan .................................. 50/150129

[51] Int. Cl.² .......................................... G01N 27/46
[52] U.S. Cl. .............................. 204/195 S; 123/119 E
[58] Field of Search .......................... 204/1 S, 195 S; 123/119 E

[56] References Cited

U.S. PATENT DOCUMENTS

| | | | |
|---|---|---|---|
| 3,691,023 | 9/1972 | Ruka et al. | 204/195 S |
| 3,841,987 | 10/1974 | Friese et al. | 204/195 S |
| 3,935,089 | 1/1976 | Togawa et al. | 204/195 S |
| 3,981,785 | 9/1976 | Sandler | 204/195 S |
| 4,005,001 | 1/1977 | Pebler | 204/195 S |

Primary Examiner—T. Tung

[57] ABSTRACT

A sensor comprising a plate of an oxygen ion conductive solid electrolyte such as stabilized zirconia, two porous electrode layers of a catalytic metal such as platinum formed on both sides of the electrolyte plate, and two porous ceramic coatings formed respectively on the two electrode layers, wherein both sides of the electrolyte plate are exposable to a gas subject to measurement through the electrode layer and the coating formed on each of them, but the total resistance offered by one of the electrode layers and the coating thereon to the permeation of the gas therethrough is different from that offered by the other electrode layer and coating, so that the gas contacts one side of the electrolyte plate with a time lag behind the contact of the gas with the other side of the plate. The sensor is useful for detecting a fluctuation in the air/fuel ratio of an air-fuel mixture fed to an internal combustion engine across the stoichiometric ratio by exposure to the exhaust gas since the fluctuation and the aforementioned time lag causes the sensor to develop an output voltage.

10 Claims, 13 Drawing Figures

SENSOR FOR DETECTING VARIATION IN OXYGEN CONCENTRATION IN GAS

This invention relates to a sensor which has a layer of an oxygen ion conductive solid electrolyte and, when both sides of the electrolyte layer are made to contact a gas containing oxygen in a variable concentration, can produce an electrical signal indicating the occurrence of a variation in the oxygen concentration. The sensor is particularly useful for detecting a fluctuation in the air/fuel ratio of an air-fuel mixture fed to an internal combustion engine through a variation in the oxygen concentration in the exhaust gas.

A conventional oxygen sensor that operates on the principle of a concentration cell has a layer of solid electrolyte in which oxygen ions work as carriers and two electron conductive and porous electrode layers are formed respectively on both sides of the electrolyte layer. A typical example of the solid electrolyte is zirconia ceramic containing a stabilizing component such as calcia, and the electrode layers are usually made of platinum. The oxygen concentration in a gas, for example exhaust gas of an internal combustion engine, is examined by exposing the two electrode layers (and hence the two sides of the electrolyte layer) of this sensor respectively to the gas subject to examination and a reference gas such as air. Then the sensor develops an electromotive force across the two electrodes according to the difference in oxygen partial pressure of the examined gas from the reference gas. This electromotive force E is determined by the Nernst's equation:

$$E = \frac{RT}{4F} \log_e \frac{P_2}{P_1} = \frac{KRT}{4F} \log_{10} \frac{P_2}{P_1} \tag{1}$$

where $R$ is the gas constant, $T$ represents the absolute temperature, $F$ is the Faraday constant, $K$ is a constant, $P$ represents oxygen partial pressure, and the subscripts 1 and 2 refer to the gas subject to measurement and the reference gas, respectively. Thus the electromotive force E or output voltage of the sensor is in dependence on temperature, so that the electrolyte layer of the sensor should be kept at an elevated temperature in practical operation.

In the exhaust gas of an internal combustion engine which is operated with a hydrocarbon fuel typified by gasoline, carbon monoxide and unburned hydrocarbons react with oxygen remaining in the exhaust gas. Accordingly the following reactions are considered to respectively be in equilibrium states in the exhaust gas.

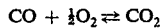

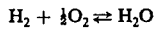

These equilibrium states and, hence, the oxygen partial pressure in the exhaust gas are in dependence on the exhaust gas temperature. Platinum is used as the material of the electrode layers of the sensor partly because of its catalytic ability on these oxidation reactions. Upon contact of the exhaust gas with the platinum electrode, these oxidation reactions rapidly proceed towards the right side. Because of the occurrence of such oxidation reactions on one side of the electrolyte layer and a great dependency of the oxygen concentration in the exhaust gas on the air/fuel ratio of an air-fuel mixture consumed in the engine, the described oxygen sensor exhibits the following output characteristic. The air/fuel ratio will hereinafter be represented by excess air factor λ which can be defined as the quotient of the air-to-fuel ratio of an air-fuel mixture consumed in the engine divided by the stoichiometric air-to-fuel ratio of the same components. The output voltage of the sensor stands at a relatively high level, only slightly affected by a variation in the air/fuel ratio (assuming that the exhaust gas temperature does not substantially vary) so long as the value of λ is smaller than 1.0 but stands at a distinctly lower level while λ is larger than 1.0. If the value of λ varies across 1.0, the output voltage exhibits an abrupt transition from one of these two levels to the other.

As is well known, an oxygen sensor of the described type is useful as a detection element in a feedback control system for controlling the air/fuel ratio of an air-fuel mixture fed to an internal combustion engine, particularly, for automotive use in connection with the prevention of air pollution and/or improvement on the fuel economy. The use of this oxygen sensor is especially advantageous when the control system aims at maintaining the excess air factor λ at or in the vicinity of 1.0 as does in many cases.

A practical construction of a conventional oxygen sensor will briefly be described with reference to part of the accompanying drawings for aiding the understanding of the present invention.

Figure 5:
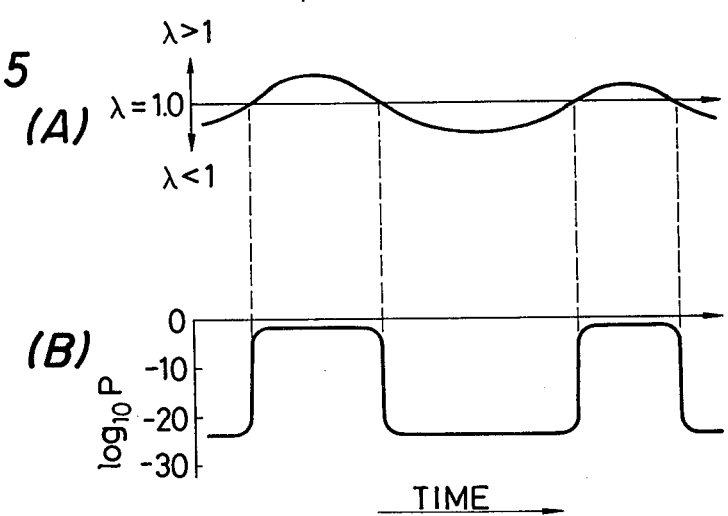
Figure 6:
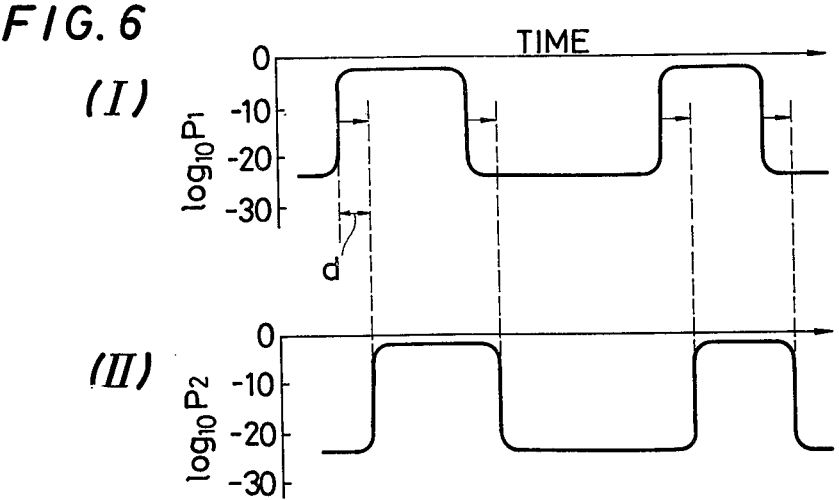
Figure 7:
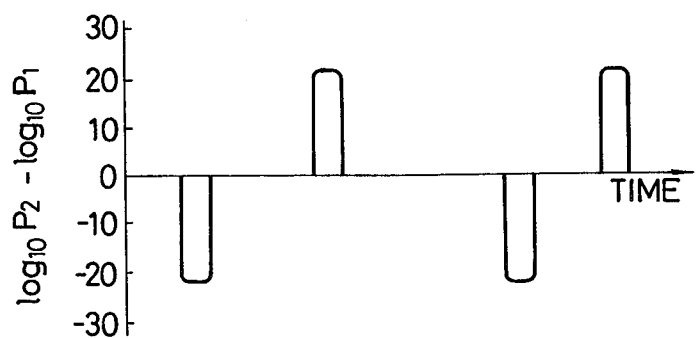
Figure 8:
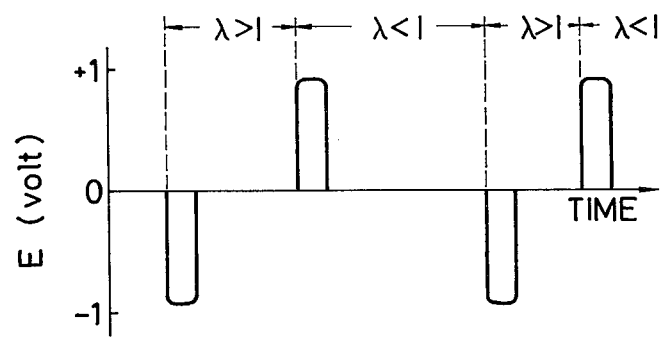
Figure 9:
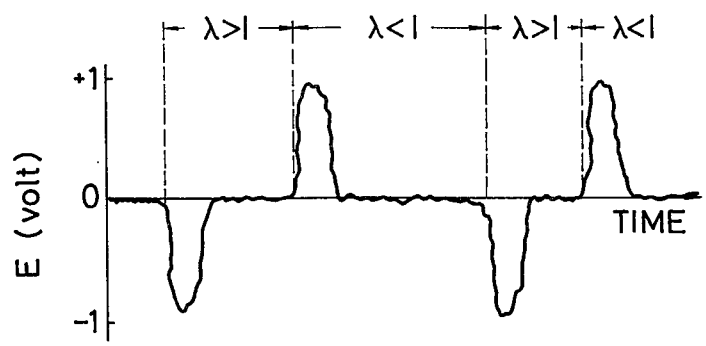
Figure 10:
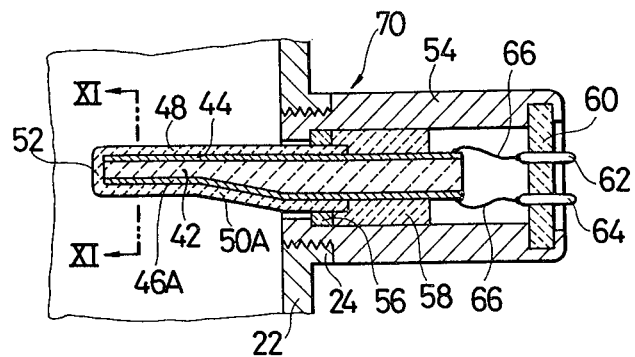
Figure 11:
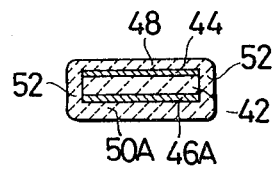
Figure 12:
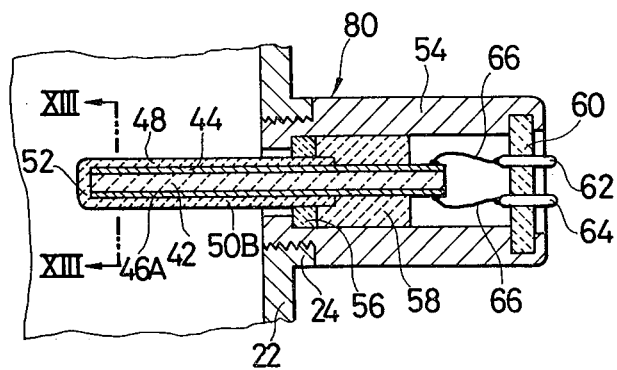
Figure 13:
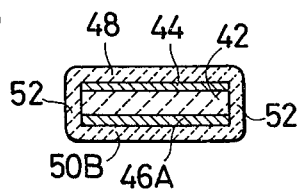

FIG. 5 presents a pair of charts showing a manner of variation in the oxygen partial pressure occurring when the air/fuel ratio exhibits a periodical fluctuation around a stoichiometric ratio;

FIG. 6 represents a pair of charts showing a time lag in the development of an oxygen partial pressure on one side of a solid electrolyte layer in a sensor according to the invention behind the development of the same oxygen partial pressure on the other side of the same layer;

FIG. 7 is a chart showing a periodical variation in the magnitude of the difference between the oxygen partial pressures on the two sides of the same electrolyte layer derived from the charts of FIGS. 5 and 6;

FIG. 8 is a chart showing a periodical fluctuation in the output voltage of the sensor resulting from the variations shown in FIG. 7;

FIG. 9 is a chart showing the same as FIG. 8 but in a form more faithful to an actual function of the sensor in a practical engine system;

FIGS. 10 and 12 are longitudinal sectional views of two differently constructed sensors, respectively, as second and third embodiments of the invention; and FIGS. 11 and 13 are cross sectional views taken along the line 11—11 of FIG. 10 and the line 13—13 of FIG. 12, respectively.

Figure 1:
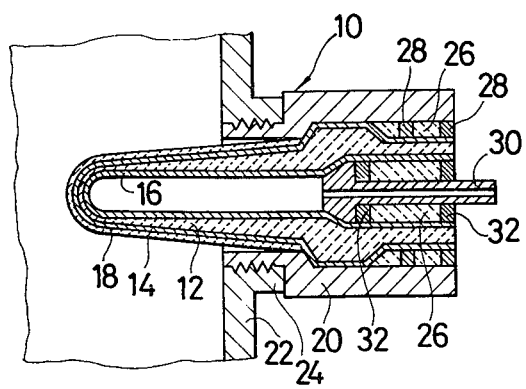
FIG. 1 is a longitudinal sectional view of a conventional oxygen sensor.

A conventional oxygen sensor 10 of FIG. 1 has a layer of an oxygen ion conductive solid electrolyte, such as zirconia stabilized with calcia, in the form of a tube 12 which is closed at one end. The outer surface of the tube 12 is entirely coated with a porous and electron conductive electrode layer 14, which is made of a metal such as platinum having a catalytic ability on the oxidation of oxidizable components of the exhaust gas of an internal combustion engine. The inner surface of the electrolyte tube 12 is entirely coated with a porous electrode layer 16 which is similar to the outer electrode layer 14 both in the material and in the structure. A porous ceramic coating 18 is formed on the outer electrode layer 14 to a thickness of about 80–120 $\mu$m for the purpose of protecting the outer electrode layer 14 against damage from direct exposure to a high velocity flow of a high temperature exhaust gas and, besides, effectively restricting the flow rate of the exhaust gas on the surface of the outer electrode layer 14 so as to allow the exhaust gas to remain in contact with the electrode layer 14 for a sufficiently long period of time and promote the achievement of an equilibrium oxygen partial pressure on the surface of the electrolyte layer 12 through the aforementioned oxidation reactions. This ceramic coating 18 is formed by a flame spraying technique, and alumina is a typical example of useful ceramic materials. The ceramic coating 18 is omitted for a portion of the outer electrode layer 14 near the open end of the electrolyte tube 12.

The thus coated electrolyte tube 12 is inserted into a tubular metal shell 20 such that a closed end portion of the tube 12 protrudes from the metal shell 20. The outside of the tube 12 and the inside of the shell 20 are shaped such that the outer electrode layer 14 is in contact with the inside of the shell 20 over a certain area. The shell 20 has on its outside a certain fixture means such as threads to air-tightly insert the protruded portion of the electrode tube 12 into an exhaust pipe 22 for an internal combustion engine, through, for example, a boss 24 formed on the wall of the exhaust pipe 22. The shell serves also as a conductor for the outer electrode layer 14. An annular space defined in the shell 20 around an open end portion of the electrolyte tube 12 is filled with an electrically conductive sealing agent 26, which is a compacted powdery material such as graphite or copper, and forcibly inserted retainer rings 28 of a metal such as copper. A tubular and flanged conductor member 30 is partially inserted into an open end portion of the bore of the electrolyte tube 12 such that the inner electrode layer 16 is in contact with the outside of the conductor member 30 over a certain area. An annular space defined in this portion of the bore of the electrolyte tube 12 around the conductor member 30 is filled with the conductive sealing agent 26 and forcibly inserted retainer rings 32 of a metal, so that the interior of the electrolyte tube 12 can communicate with the atmosphere only through the bore of the conductor member 30.

In use of this oxygen sensor 10, the exhaust gas comes into contact with the outside of the electrolyte tube 12 through the ceramic coating 18 and the outer electrode layer 14, while the inside of the electrolyte tube 12 is completely isolated from the exhaust gas and is exposed to atmospheric air as a reference gas through the inner electrode layer 16.

Conventional oxygen sensors typified by the sensor 10 of FIG. 1 generally have the following disadvantages.

(1) A hermetic and heat-resistant seal is indispensable to the sensors for completely isolating one side of the electrolyte layer from the exhaust gas.

(2) Accordingly the electrolyte layer and/or the shell of the sensors are inevitably complicated in shape, resulting in complicated construction of the sensors.

(3) The sensors become inoperable when the electrolyte layer, which is not very tough, cracks due to, for example, thermal shocks.

(4) Since the electrolyte layer is heated by the exhaust gas only from the outside, the electrolyte layer cannot readily and uniformly be heated to a desirable temperature and is subjected to thermal stresses.

It is an object of the present invention to provide an improved sensor for detecting a fluctuation in the concentration of oxygen in a gas stream, which sensor utilizes a layer of a known oxygen ion conductive solid electrolyte as a principal element but is free from the above described disadvantages of conventional oxygen sensors.

It is another object of the invention to provide a sensor which can produce, when exposed to exhaust gas of an internal combustion engine, an electrical signal clearly indicating a fluctuation in the air/fuel ratio of an air-fuel mixture consumed in the engine across the stoichiometric air/fuel ratio.

A sensor according to the invention comprises a layer of an oxygen ion conductive solid electrolyte, a support means for supporting the electrolyte layer such that at least a portion of the electrolyte layer can be exposed on both sides thereof to a stream of a gas containing oxygen and oxidizable components, first and second porous and electron conductive electrode layers of a metal having catalytic ability on oxidation reactions of oxidizable components of the gas formed respectively on first and second sides of the electrolyte layer, and first and second porous protective coatings formed respectively on the first and second electrode layers at least in regions exposable to the gas stream. The two electrode layers and/or the two protective coatings are formed such that the total resistance offered by the first protective coating and the first electrode layer to the permeation of the gas therethrough is different from the total resistance offered by the second protective coating and the second electrode layer to the permeation of the gas therethrough, so that the gas comes into contact with one side of the electrolyte layer with a time lag behined the contact of the gas stream with the other side of the electrolyte layer.

The above described two different resistances to the passing of the gas can be offered by forming the first and second electrode layers to two different thicknesses, by forming the first and second protective coatings to two different thicknesses and/or by forming the first and second protective coatings to be different from each other in the total pore volume thereof.

The materials of the respective elements of a sensor according to the invention are identical with those which are employed in conventional oxygen sensors of the hereinbefore described oxygen concentration cell type. The first and second protective coatings are preferably joined with each other by coating the side faces of the electrolyte layer with the same material as that of these protective coatings.

In a stream of exhaust gas of an internal combustion engine, this sensor produces an output voltage when the air/fuel ratio of the air-fuel mixture fluctuates across the stoichiometric ratio and a difference arises between oxygen partial pressure on one side of the electrolyte layer and that on the other side due to both a fluctuation in the oxygen concentration in the exhaust gas stream and the aforementioned time lag. The direction of the fluctuation in the air/fuel ratio, that is, whether the fluctuation is from a range below the stoichiometric ratio to a range above the stoichiometric ratio or contrary, can clearly be identified from the polarity of the output voltage of the sensor: the output voltage is a negative one in the former case but positive in the latter case.

The invention will fully be understood from the following detailed description of preferred embodiments with reference to the drawings.

Figure 2:
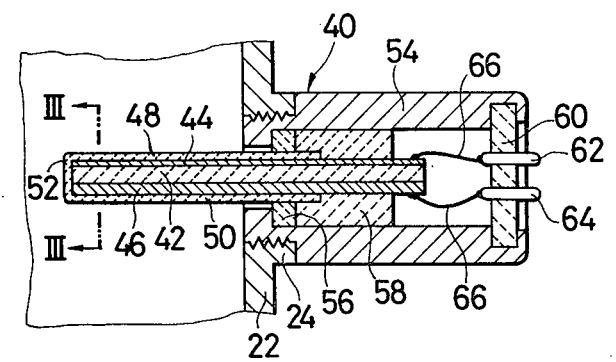
FIG. 2 is a longitudinal sectional view of a sensor as a first embodiment of the invention.
Figure 3:
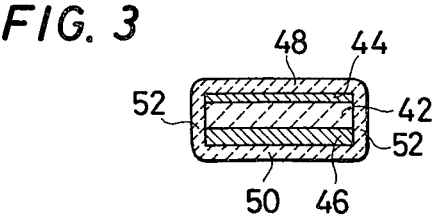
FIG. 3 is a cross sectional view taken along the line 3—3 of FIG. 2.

Referring now to FIGS. 2 and 3, a sensor 40 as a first embodiment of the invention has a layer of an oxygen ion conductive solid electrolyte, such as zirconia ceramic containing calcia as a stabilizing component, in the form of a rectangular plate 42. A porous and electron conductive first electrode layer 44 is formed on one side of the electrolyte plate 42 (this side will be referred to as the first side), and a second electrode layer 46 which is similar to the first electrode layer 42 both in the material and in structure is formed on the reverse side (will be referred to as the second side) of the electrolyte plate 42. These electrode layers 44 and 46 are essentially similar to the electrode layers 14 and 16 in the conventional oxygen sensor 10 of FIG. 1: they are formed by applying a paste containing a catalytic metal powder such as platinum powder dispersed therein onto the first and second sides of the electrolyte plate 42 and baking the applied paint. The electrode layers 44, 46 have micropores or interstices which are communicating with one another and accordingly are permeable to gases. In this sensor 40, the second electrode layer 46 is substantially thicker than the first electrode layer 44.

To stationarily dispose a portion of the electrolyte plate 42 with the electrode layers 44, 46 thereon in the exhaust pipe 22, the sensor 40 has a tubular metal shell 54 having threads on its outside for attachment to the boss 24. A ceramic disk 56 having a rectangular slot is fixedly received in an end portion of the metal shell 54, and the electrolyte plate 42 is passed through the slot of this ceramic disk 56 such that the electrolyte plate 42 partly protrudes from the shell 54 into the exhaust pipe 22 and is partly enclosed in the shell 54, spaced from the wall of the shell 54. The interior of the shell 54 is partly filled with a heat-resistant and electrically nonconductive filler 58 such as a ceramic cement to prevent movement of the electrolyte plate 42 and the ceramic disk 56 relatively to the shell 54. A closure disk 60 of an electrically nonconductive material such as, for example, ceramic is fixed to the shell 54 to cover its open end by, for example, circumferentially crimping the end portion of the shell 54. An end portion of the electrolyte plate 42 protrudes from the filler 58 into a space defined in the shell 54 between the filler 58 and the closure disk 60. The filler 58 serves also as a sealing agent for preventing the inflow of the exhaust gas into this space. First and second terminal pins 62 and 64 pass through the closure disk 60 and are connected respectively to the first and second electrode layers 44 and 46 by leads 66 of, for example, platinum wire.

Previous to the joining of the electrolyte plate 42 with the shell 54, first and second protective coatings 48 and 50 of a ceramic material are formed respectively on the first and second electrode layers 44 and 46. These protective coatings 48 and 50 are porous and permeable to gases. Similarly to the protective coating 18 in the conventional oxygen sensor 10 of FIG. 1, these ceramic coatings 48 and 50 are formed by flame-spraying a powdered ceramic material typified by alumina. In the sensor 40 of FIG. 2, the first and second ceramic coatings 48 and 50 are identical in the material, thickness and porosity. Preferably, these two coatings 48 and 50 are joined together or made to be a single layer by coating side faces of the electrolyte plate 42 with substantially the same ceramic layer 52. The ceramic coatings 48 and 50 are omitted for end regions of the first and second electrode layers 44 and 46, which regions are to be positioned in the open space in the shell 54.

When the thus constructed sensor 40 is attached to the exhaust pipe 22 as shown in FIG. 2, and the exhaust gas streams through the pipe 22, the exhaust gas arrives on the first side of the electrolyte plate 42 through the first ceramic coating 48 and the first electrode layer 44. Unlike the conventional oxygen sensor 10 of FIG. 1, this sensor 40 allows the exhaust gas to arrive also on the second side of the electrode plate 42 through the second ceramic coating 50 and the second electrode layer 46. However, the second electrode layer 46 has a larger thickness than the first electrode layer 44 and accordingly offers a greater resistance to the permeation of the exhaust gas therethrough than the first electrode layer 44 does. As a result, the exhaust gas arrives on the second side of the electrolyte plate 42 with a time lag behind the contact of the exhaust gas with the first side of the electrolyte plate 42. If the partial pressure of oxygen in the exhaust gas stream exhibits a variation, therefore, there arises a difference between an oxygen partial pressure on the first side of the electrolyte plate 42 at a certain moment and that on the second side at the same moment. Then the sensor 40 produces an output voltage as explained below more in detail.

Figure 4:
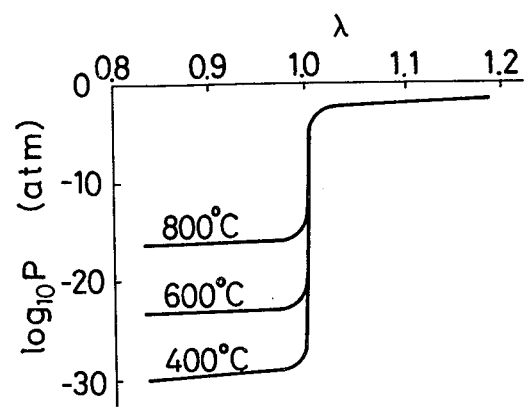
FIG. 4 is a graph showing the relationship between the air/fuel ratio of an air-fuel mixture consumed in an internal combustion engine and the oxygen partial pressure in the exhaust gas of the engine.

When an exhaust gas resulting from the combustion of an air-gasoline mixture in an internal combustion engine is contacted with a catalytic metal such as platinum at an elevated temperature, an equilibrium partial pressure of oxygen P(atm) in the exhaust gas varies with variations in the air/fuel ratio, i.e., excess air factor $\lambda$, of the mixture and the exhaust gas temperature in a manner as shown in FIG. 4. The oxygen partial pressure stands at two distinctly different levels according as the value of $\lambda$ remains on either side of 1.0 where the air/fuel ratio is stoichiometric. At 600° C, for example, the oxygen partial pressure P is on the order of $10^{-20}$ while the value of $\lambda$ is smaller than 1.0 but on the order of $10^{-20}$ while $\lambda$ is larger than 1.0. The oxygen partial pressure P exhibits an abrupt transition from one of these two levels to the other when $\lambda$ varies across 1.0.

The operation of a feedback control system for maintaining the value of $\lambda$ at 1.0 will result in a small magnitude of periodical fluctuation of $\lambda$ around and across 1.0 as typified by the chart (A) of FIG. 5. On the basis of this chart (A) and the graph of FIG. 4, the oxygen partial pressure P in the exhaust gas (upon contact with platinum) at 600° C exhibits a periodical fluctuation in a manner as shown by the chart (B) of FIG. 5.

If the sensor 40 according to the invention is exposed to a stream of the exhaust gas in which the oxygen partial pressure P fluctuates as shown in FIG. 5, the fluctuating oxygen partial pressure P is applied onto the first side of the electrolyte plate 42. For the first side of the electrolyte plate 42, an oxygen partial pressure will hereinafter be represented by $P_1$ for convenience in explanation. In FIG. 6, the chart (I), which is substantially identical with the chart (B) of FIG. 5, shows the fluctuation in the oxygen partial pressure $P_1$ in the exhaust gas stream on the outside of the electrolyte plate 42. The exhaust gas passes through the second electrode layer 46 too and arrives on the second side of the electrolyte plate 42 with a time lag behind the arrival of the same exhaust gas on the first side of the plate 42 as described hereinbefore. For the second side of the plate 42, an oxygen partial pressure will hereinafter be represented by $P_2$. Since the oxygen partial pressure $P_1$ exhibits a periodical fluctuation as shown in the chart (I), also $P_2$ exhibits a fluctuation fundamentally in the same manner. However, there is a phase difference between the fluctuation of $P_1$ and that of $P_2$ due to the aforementioned time lag. In contrast to the chart (I), the periodical fluctuation of $P_2$ is shown by the chart (II) of FIG. 6. The magnitude of the phase difference between the curve of the chart (II) or the amount of the time lag is indicated at $d$ in FIG. 6.

When the amount of the time lag $d$ (which depends on the magnitude of the thickness difference between the first and second electrode layers 44 and 46) is appropriately preset in relation to the frequency of the periodical fluctuation in the oxygen partial pressure P or fluctuation in the value of $\lambda$, there arises a difference between the magnitudes of $P_1$ and $P_2$ intermittently for certain periods of time as seen in FIG. 6. The EMF or output voltage E of the sensor 40 is given by the following equation:

$$E = \frac{KRT}{4F} \log_{10}\frac{P_2}{P_1} \quad (2)$$
$$= \frac{KRT}{4F} (\log_{10}P_2 - \log_{10}P_1)$$

The value of $(\log_{10}P_2 - \log_{10}P_1)$ calculated from the charts of FIG. 6 exhibits a periodical fluctuation as shown in FIG. 7.

FIG. 8 shows a similar fluctuation of the output voltage E(volts) as the result of a numerical calculation on the equation (2) based on the chart of FIG. 7. As seen in FIG. 8, the output voltage E of the sensor 40 takes a value of about $-1$ volt when the value of $\lambda$ varies across 1.0 from a smaller range ($\lambda < 1.0$, meaning the presence of excess fuel in the air-fuel mixture) to a larger range ($\lambda > 1.0$, meaning shortage of fuel in the mixture) but another value of about $+1$ volt when $\lambda$ varies across 1.0 from a larger range to a smaller range. The output voltage E remains substantially at zero volt while the value of $\lambda$ remains either above or below 1.0. The output voltage E varies depending on the exhaust gas temperature as demonstrated in FIG. 4, but exhibits a periodical fluctuation in a manner as shown in FIG. 8 regardless of the exhaust gas temperature so long as the value of $\lambda$ varies across 1.0. It will be understood that the waveform in FIG. 8 is an idealized one and that an actual waveform of the output voltage E in practical use of the sensor 40 is somewhat deformed and/or rippled as shown in FIG. 9 because of minute and continual variations in various factors including the value of $\lambda$.

Due to the above described output characteristic, the sensor 40 is not suitable for exactly measuring the oxygen concentration in the exhaust gas but is quite suitable for examining whether the air/fuel ratio of a combustible mixture consumed in the engine varies across the stoichiometric air/fuel ratio or not. Accordingly the sensor 40 is useful as an element for providing a feedback signal in a control system for maintaining the air/fuel ratio at or in the vicinity of the stoichiometric ratio. As one of the advantages of the sensor 40, whether the amount of fuel in the air-fuel mixture has varied from excess to shortage or can easily and doubtless be identified since the polarity of the output voltage of the sensor 40 varies depending on the direction of the transition of the excess air factor $\lambda$ across 1.0.

In a sensor 70 shown in FIGS. 10 and 11 as a second embodiment of the invention, the first electrode layer 44 is formed on the first side of the electrolyte plate 42 in the same manner as in the sensor 40 of FIG. 2, but a second electrode layer 46A is formed on the second side of the plate 42 to have the same thickness as the first electrode layer 44. In FIG. 10, the electrolyte plate 42 is not uniform in thickness but has a reduced thickness in a region to be exposed to the exhaust gas. This shape is employed for minimizing the internal impedance of the electrolyte plate 42 without significantly sacrificing its physical strength. The sensor 40 of FIG. 2 and a sensor 80 of FIG. 12 (will be described later) also may have the thus shaped electrolyte plate 42. The first ceramic coating 48 is formed on the first electrode layer 44 in the same manner as in the sensor 40 of FIG. 2. A second ceramic coating 50A, which is essentially similar to the first ceramic coating 48, is formed on the second electrode layer 46A to have a substantially larger thickness than the first ceramic coating 48. The first and second coatings 48 and 50A are preferably joined together by the ceramic coating 52 formed on the side faces of the electrolyte plate 42. In other respects, this sensor 70 is identical with the sensor 40 of FIG. 2.

In this sensor 70, the second ceramic coating 50A offers a greater resistance to the permeation of the exhaust gas therethrough due to its larger thickness than the first ceramic coating 48 does. Meanwhile, the first and second electrode layers 44 and 46A offer the same resistance to the permeation of the exhaust gas therethrough. Consequently, the exhaust gas arrives on the second side of the electrolyte plate 42 with a time lag behind its arrival on the first side. Thus, this sensor 70 has the same function or output characteristic as the sensor 40 of FIG. 2 has.

FIGS. 12 and 13 show a still different sensor 70 as a third embodiment of the invention. This sensor 80 is generally identical with the sensor 70 of FIG. 10, but the second electrode layer 46A is coated with a ceramic coating 50B which is different not only from the first ceramic coating 48 but also from the second ceramic coating 50A in FIG. 10. The second ceramic coating 50B is porous and permeable to gas and has substantially the same thickness as the first ceramic coating 48. However, the total pore volume of the second ceramic coating 50B is smaller than that of the first ceramic coating 48. The total pore volume is reduced by making the individual pores or interstices smaller and/or lessening the number of the pores per unit volume of the ceramic coating. The pore size and/or the pore density in the ceramic coating can be varied by varying the temperature for the flame spraying. The reduced total pore volume for the second ceramic coating 50B may be achieved either over the entire volume of the coating 50B or only in an outer surface region. The first and second ceramic coatings 48 and 50B are preferably joined together by the ceramic coating 52 formed on the side faces of the electrolyte plate 42.

Since the reduced total pore volume of the second ceramic coating 50B means an augmented resistance to the permeation of the exhaust gas therethrough, the sensor 80 exhibits the same output characteristic as the hereinbefore described sensors 40 and 70.

The above described three different methods of realizing a two different levels of resistance to the permeation of the exhaust gas, (1) forming the two porous electrode layers to different thicknesses, (2) forming the two porous protective coatings to different thicknesses and (3) forming the two porous protective coatings to different porosities, may be employed by twos in any combination or even all simultaneously.

In an air/fuel ratio control system, one of the terminal pins 62 and 64 of the sensor 40, 70 or 80, for example the first terminal pin 62, may electrically be connected to the exhaust pipe 22 through the metal shell 54 on condition that a negative terminal of the control circuit is connected to the exhaust pipe 22 and that the second terminal pin 64 is connected to a positive terminal of the control circuit. Such a connection method is frequently employed in air/fuel ratio control systems including a conventional oxygen sensor for minimizing the wiring cost. In this case, only a very small current flows through the ground lines connected to the exhaust pipe 22 since the control circuit is made to have a high input impedance to match with a high impedance of the electrolyte plate 42 at low temperatures. Accordingly, the control circuit fails in its function if the ground line connecting the first terminal pin 62 to the exhaust pipe 22 has an unduly high resistance. Inconveniently, the exhaust pipe 22 is liable to suffer rust or oxidation on its surface since the exhaust pipe 22 is frequently splashed with water and experiences a severe temperature change, resulting in a significant increase in the contact resistance between the shell 54 and the exhaust pipe 22. To preclude the failure in the function of the control circuit caused by such increase in the resistance of the ground lines, the first terminal pin 62 is preferably connected directly to a negative terminal of the control circuit whether the same pin 62 is connected to the exhaust pipe or not.

Other than the unique output characteristic as described hereinbefore, a sensor according to the invention has the following advantages as an element to be exposed to an exhaust gas stream.

(1) The sensor has a simplified construction and involves a less significant problem about a hermetic and heat-resistant seal compared with conventional oxygen sensors. Accordingly the sensor can easily be mass-produced.

(2) The solid electrolyte layer of the sensor can readily and uniformly be heated by the exhaust gas since the heat is supplied from both sides of the electrolyte layer.

(3) The electrolyte layer has a less chance of cracking through thermal stresses and can operate even if it cracks to a certain extent.

A sensor according to the invention is useful also for detecting the occurrence of a fluctuation in the concentration of oxygen in other various types of gases, particularly combustion gases produced by combusters other than internal combustion engines.

What is claimed is:

1. A sensor for detecting the occurrence of a fluctuation in the air/fuel ratio of an air-fuel mixture fed to an internal combustion engine across the stoichiometric air/fuel ratio by disposing the sensor in a stream of the exhaust gas of the engine, the sensor comprising:

a layer of an oxygen ion conductive solid electrolyte;
a support means for supporting the solid electrolyte layer such that at least a portion of said solid electrolyte layer can be exposed on both sides thereof to a stream of the exhaust gas;

porous and electron conductive first and second electrode layers of a metal having catalytic ability on oxidation reactions of carbon monoxide and hydrocarbons contained in the exhaust gas formed respectively on first and second sides of said solid electrolyte layer at least in regions exposable to the exhaust gas stream; and porous first and second protective coatings of a refractory material formed respectively on said first and second electrode layers at least in regions exposable to the exhaust gas stream;

said first and second electrode layers and said first and second protective coatings being formed such that the total resistance offered by said first protective coating and said first electrode layer to the permeation of the exhaust gas therethrough is different from the total resistance offered by said second protective coating and said second electrode layer to the permeation of the exhaust gas therethrough, so that the exhaust gas comes into contact with said second side of said solid electrolyte layer with a time lag behind the contact of the exhaust gas stream with said first side of said solid electrolyte layer whereby establishing an electromotive force when a fluctuation occurs in the oxygen partial pressure of the exhaust gas resulting from a fluctuation in said air/fuel ratio, across said stoichiometric ratio, with the polarity of said electromotive force indicating whether the air/fuel ratio is increasing or decreasing.

2. A sensor as claimed in claim 1, wherein said solid electrolyte layer takes the form of a flat plate, said support means including a tubular shell which receives therein a portion of said electrolyte layer such that said electrode layer is exposable to the exhaust gas stream in a portion protruding from one end of said shell.

3. A sensor as claimed in claim 2, wherein said support means further include a holder plate of a heat-resistant and electrically nonconductive material fixedly received in said shell to close said one end of said shell, said holder plate having a slot shaped such that said solid electrolyte layer passes through said slot and lies generally normal to said holder plate, and an electrically nonconductive filler filling in a portion of the interior of said shell to cover said holder plate and prevent said electrolyte layer from moving relatively to said shell.

4. A sensor as claimed in claim 2, further comprising a third protective coating of the same material as said first and second protective coatings formed on side faces of said electrolyte layer at least in a portion thereof protruding from said shell to join said first and second protective coatings with each other.

5. A sensor as claimed in claim 2, wherein said solid electrolyte is zirconia containing calcia as a stabilizing component and said first and second electrode layers are made of platinum.

6. A sensor for detecting the occurrence of a fluctuation in the air/fuel ratio of an air-fuel mixture fed to an internal combustion engine cross the stoichiometric air/fuel ratio by disposing the sensor in a stream of the exhaust gas of the engine, the sensor comprising:

a layer of an oxygen ion conductive solid electrolyte;
a support means for supporting the solid electrolyte layer such that at least a portion of said solid electrolyte layer can be exposed on both sides thereof to a stream of the exhaust gas;

a porous and electron conductive first electrode layer of a metal having catalytic ability on oxidation reactions of carbon monoxide and hydrocarbons contained in the exhaust gas formed on a first side of said solid electrolyte layer at least in a region exposable to the exhaust gas stream;

a porous and electron conductive second electrode layer of said metal formed on a second side of said solid electrolyte layer at least in said region with a larger thickness than said first electrode layer and substantially the same porosity as said first electrode layer; and porous first and second protective coatings of the same one refractory material formed respectively on said first and second electrode layers with the same thickness;

whereby, when the sensor is exposed to the exhaust gas stream, establishing an electromotive force when a fluctuation occurs in the oxygen partial pressure of the exhaust gas resulting from a fluctuation in said air/fuel ratio, across said stoichiometric ratio, with polarity of said electromotive force indicating whether the air/fuel ratio is increasing or decreasing.

7. A sensor for detecting the occurrence of a fluctuation in the air/fuel ratio of an air-fuel mixture fed to an internal combustion engine across the stoichiometric air/fuel ratio by disposing the sensor in a stream of the exhaust gas of the engine, the sensor comprising:

a layer of an oxygen ion conductive solid electrolyte;

a support means for supporting the solid electrolyte layer such that at least a portion of said solid electrolyte layer can be exposed on both sides thereof to a stream of the exhaust gas;

porous and electron conductive first and second electrode layers of a metal having catalytic ability on oxidation reactions of carbon monoxide and hydrocarbons contained in the exhaust gas formed respectively on first and second sides of said solid electrolyte layer at least in regions exposable to the exhaust gas stream; and a porous first protective coating of a refractory material formed on said first electrode layer; and a porous second protective coating of said refractory material formed on said second electrode layer with substantially the same porosity as said first protective coating and a larger thickness than said first protective coating;

whereby, when the sensor is exposed to the exhaust gas stream, establishing an electromotive force when a fluctuation occurs in the oxygen partial pressure of the exhaust gas resulting from a fluctuation in said air/fuel ratio, across said stoichiometric ratio, with the polarity of said electromotive force indicating whether the air/fuel ratio is increasing or decreasing.

8. A sensor for detecting the occurrence of a fluctuation in the air/fuel ratio of an air-fuel mixture fed to an internal combustion engine across the stoichiometric air/fuel ratio by disposing the sensor in a stream of the exhaust gas of the engine, the sensor comprising:

a layer of an oxygen ion conductive solid electrolyte;

a support means for supporting the solid electrolyte layer such that at least a portion of said solid electrolyte layer can be exposed on both sides thereof to a stream of the exhaust gas;

porous and electron conductive first and second electrode layers of a metal having catalytic ability on oxidation reactions of carbon monoxide and hydrocarbons contained in the exhaust gas formed respectively on first and second sides of said solid electrolyte layer at least in regions exposable to the exhaust gas stream; and a porous first protective coating of a refractory material formed on said first electrode layer; and a porous second protective coating of said refractory material formed on said second electrode layer with the same thickness as said first protective coating and a smaller total pore volume than said first protective coating, whereby, when the sensor is exposed to the exhaust gas stream, establishing an electromotive force when a fluctuation occurs in the oxygen partial pressure of the exhaust gas resulting from a fluctuation in said air/fuel ratio, across said stoichiometric ratio, with the polarity of said electromotive force indicating whether the air/fuel ratio is increasing or decreasing.

9. A sensor as claimed in claim 8, wherein individual pores of said second protective coating are smaller in size than individual pores of said first protective coating.

10. A sensor as claimed in claim 8, wherein the number of pores per unit volume in said second protective coating is smaller than that in said first protective coating.

* * * * *